(12) United States Patent
Prior

(10) Patent No.: US 11,065,051 B2
(45) Date of Patent: Jul. 20, 2021

(54) SPECIMEN RETRIEVAL DEVICE

(71) Applicant: Covidien LP, Mansfield, MA (US)

(72) Inventor: Scott J. Prior, Shelton, CT (US)

(73) Assignee: COVIDIEN LP, Mansfield, MA (US)

(*) Notice: Subject to any disclaimer, the term of this patent is extended or adjusted under 35 U.S.C. 154(b) by 324 days.

(21) Appl. No.: 16/126,345

(22) Filed: Sep. 10, 2018

(65) Prior Publication Data

US 2019/0133677 A1     May 9, 2019

Related U.S. Application Data

(60) Provisional application No. 62/581,171, filed on Nov. 3, 2017.

(51) Int. Cl.
| | | |
|---|---|---|
| *A61B 18/14* | (2006.01) | |
| *A61B 17/00* | (2006.01) | |
| *A61B 17/34* | (2006.01) | |
| *A61B 18/00* | (2006.01) | |

(52) U.S. Cl.
CPC .... *A61B 18/1487* (2013.01); *A61B 17/00234* (2013.01); *A61B 17/3421* (2013.01); *A61B 2017/00287* (2013.01); *A61B 2017/3454* (2013.01); *A61B 2018/00077* (2013.01); *A61B 2018/00601* (2013.01); *A61B 2018/142* (2013.01)

(58) Field of Classification Search
CPC .... A61B 17/00234; A61B 2017/00287; A61B 2018/00601
See application file for complete search history.

(56) References Cited

U.S. PATENT DOCUMENTS

| | | |
|---|---|---|
| 30,471 A | 10/1860 | Dudley |
| 31,564 A | 5/1862 | Logan et al. |
| 156,477 A | 11/1874 | Bradford |
| 1,609,014 A | 11/1926 | Dowd |
| 3,800,781 A | 4/1974 | Zalucki |

(Continued)

FOREIGN PATENT DOCUMENTS

| | | |
|---|---|---|
| DE | 3542667 A1 | 6/1986 |
| DE | 8435489 U1 | 8/1986 |

(Continued)

OTHER PUBLICATIONS

Matthew Bin Han Ong, "FDA Allows Containment Bags for Power Morcellators; Paper Reports Leakage", Apr. 18, 2016, The Cancer Letter, pp. 1-9. (Year: 2016).*

(Continued)

*Primary Examiner* — Christine H Matthews
(74) *Attorney, Agent, or Firm* — Carter, DeLuca & Farrell LLP

(57) ABSTRACT

A specimen retrieval device for extraction of tissue includes a port having a specimen bag attached thereto. The specimen bag includes two openings: one opening attached to the port, and the other opening spaced from the first opening, which may remain open in a patient's body to permit introduction of a tissue specimen therein. The second opening may be closed after introduction of a tissue specimen into the specimen bag, and the tissue within the specimen bag may be broken up as it is passes out of the specimen bag and through the port of the specimen retrieval device.

17 Claims, 5 Drawing Sheets

(56) References Cited

U.S. PATENT DOCUMENTS

| | | |
|---|---|---|
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |

(56) References Cited

U.S. PATENT DOCUMENTS

| | | |
|---|---|---|
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2017/0049427 A1 | 2/2017 | Do et al. |
| 2017/0215904 A1 | 8/2017 | Wassef et al. |
| 2017/0224321 A1 | 8/2017 | Kessler et al. |
| 2018/0049771 A1* | 2/2018 | Rhemrev-Pieters ... A61B 90/40 |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |

OTHER PUBLICATIONS

Hanh Tran, "Safety and Efficacy of Single Incision Laparoscopic Surgery for Total Extraperitoneal Inguinal Hernia Repair", 2011, JSLS, 15:47-52. (Year: 2011).*
European Search Report EP 12191639.9 dated Feb. 20, 2013.
European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.

(56) References Cited

OTHER PUBLICATIONS

European Search Report EP 12189517.1 dated Mar. 6, 2013.
European Search Report EP 12158873 dated Jul. 19, 2012.
European Search Report EP 11250836 dated Sep. 12, 2013.
International Search Report issued in corresponding Appl. No. PCT/US2018/058609 dated Feb. 22, 2019.

* cited by examiner

SPECIMEN RETRIEVAL DEVICE

CROSS-REFERENCE TO RELATED APPLICATION

This application claims the benefit of and priority to U.S. Provisional Patent Application No. 62/581,171 filed Nov. 3, 2017, the entire disclosure of which is incorporated by reference herein.

TECHNICAL FIELD

The present disclosure relates to a retrieval device and, more particularly, to a surgical retrieval device for removing tissue specimens from an internal body cavity.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of a body cavity. The surgeon can then perform diagnostic and/or therapeutic procedures at the surgical site with the aid of specialized instrumentation, such as forceps, graspers, cutters, applicators, and the like, which are designed to fit through additional cannulas.

When removing certain tissues from the body cavity, for example tumor tissue, it is important that the tumor tissue does not come into contact with healthy or uninvolved tissue. If tumor tissue or tissue parts have to be removed, they may be introduced into an "containment bag," also referred to herein as a "specimen bag," at the site where the tumor or diseased tissue has been detached from the surrounding tissue, after which the specimen bag is withdrawn from the body, thereby minimizing contact of the diseased tissue with healthy tissue.

Improved retrieval devices for use in minimally invasive surgical procedures remain desirable.

SUMMARY

The present disclosure is directed to surgical apparatuses and kits for use in minimally invasive surgery. In embodiments, the present disclosure provides a specimen retrieval device including a port defining a longitudinal bore and a channel, the port possessing a proximal portion, a distal portion, and a cutting element at the distal portion. Specimen retrieval devices of the present disclosure also include a specimen bag defining a reservoir and having a first opening at a proximal portion of the specimen bag and a second opening spaced from the first opening, the first and second openings communicating with the reservoir, the first opening affixed to and in fluid communication with the distal portion of the port, and the second opening defined by a mouth of the specimen bag.

In embodiments, the shape of the cutting element may be u-shaped, circular, partially circular, oblong, square, rectangular, or triangular. In some embodiments, the cutting element possesses a u-shape.

In embodiments, the cutting element is formed of an electrically conductive material and is attached to electrical leads.

In some embodiments, the distal portion of the port is attached to the cutting element by a method including adhesive bonding, welding, heat-sealing, or combinations thereof.

In other embodiments, the distal portion of the port is attached to the first opening of the specimen bag by a method including adhesive bonding, welding, heat-sealing, or combinations thereof.

In some embodiments, the port has a proximal portion including a flange.

A kit of the present disclosure includes a specimen retrieval device as described herein and at least one additional component, such as trocars, graspers, scalpels, vacuum tubes, inflation sources, or combinations thereof.

Methods of the present disclosure include, in embodiments, introducing a specimen retrieval device into a body opening such that a port of the specimen retrieval device extends through the body opening, and a specimen bag having a first opening affixed to and in fluid communication with a distal portion of the port is positioned within a body cavity. The method also includes passing a tissue specimen through a second opening of the specimen bag into the specimen bag, the second opening spaced from the first opening, and contacting the tissue specimen with a cutting element on the port as the tissue specimen is removed from the specimen bag through the port.

In embodiments, a grasper is used to contact the tissue specimen with the cutting element and remove the tissue specimen through the port. In some embodiments, the method also includes manipulating the port, the grasper, or both, to preserve continuity of the tissue specimen as it passes through the port. For example, in embodiments, the port is manipulated by rotating the port along its longitudinal axis. In other embodiments, the grasper is manipulated by laterally deflecting the grasper within the longitudinal bore of the port.

In some embodiments, methods of the present disclosure also include, prior to removing the tissue specimen through the port, introducing a second port through a second body opening and introducing a grasper through the second port into the body cavity. The grasper is used to grasp a mouth defining the second opening of the specimen bag and the mouth and the second opening of the specimen bag are removed through the second port to close off the specimen bag from the body cavity.

BRIEF DESCRIPTION OF THE DRAWINGS

Embodiments of the presently disclosed specimen retrieval device are described herein with reference to the drawings wherein.

DETAILED DESCRIPTION

Figure 1:
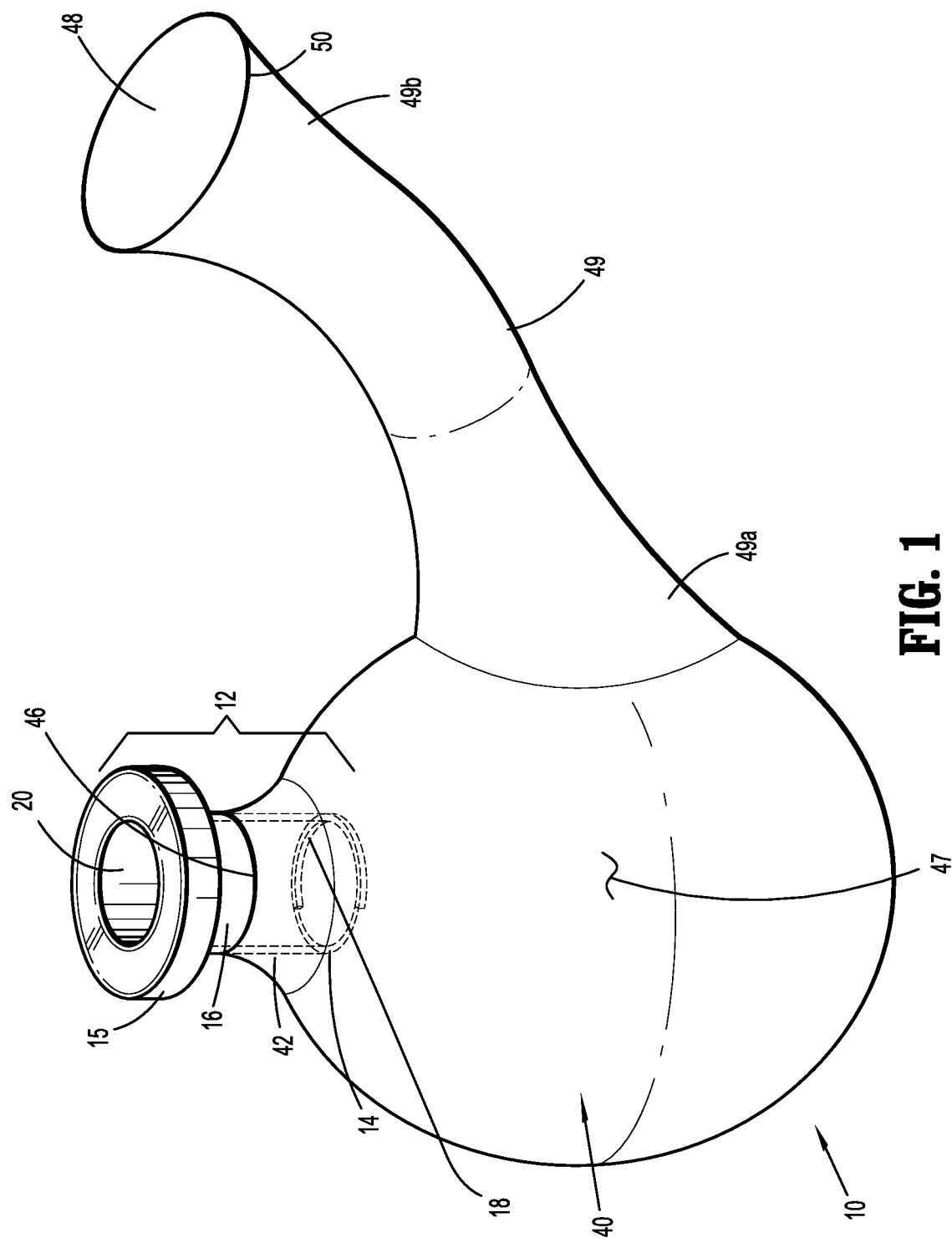
FIG. 1 is a perspective view of a specimen retrieval device in accordance with the present disclosure.

The present disclosure provides a specimen retrieval device for use in minimally invasive surgical procedures. As used herein with reference to the present disclosure, minimally invasive surgical procedures encompass laparoscopic procedures and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

As used herein, the term "distal" refers to that portion of a specimen retrieval device which is farthest from the user, while the term "proximal" refers to that portion of the specimen retrieval device of the present disclosure which is closest to the user.

The present disclosure provides a specimen retrieval device including a port having a specimen bag attached thereto. The port has a cutting element, in embodiments in the shape of a U-shaped partial ring, capable of cutting tissue during placement of the port, as well as cutting tissue being removed from the specimen bag through the port.

Embodiments of the present disclosure will now be described in detail with reference to the drawings, in which like reference numerals designate identical or corresponding elements in each of the several views. In the following description, well-known functions or constructions are not described in detail to avoid obscuring the present disclosure in unnecessary detail.

Figure 2:
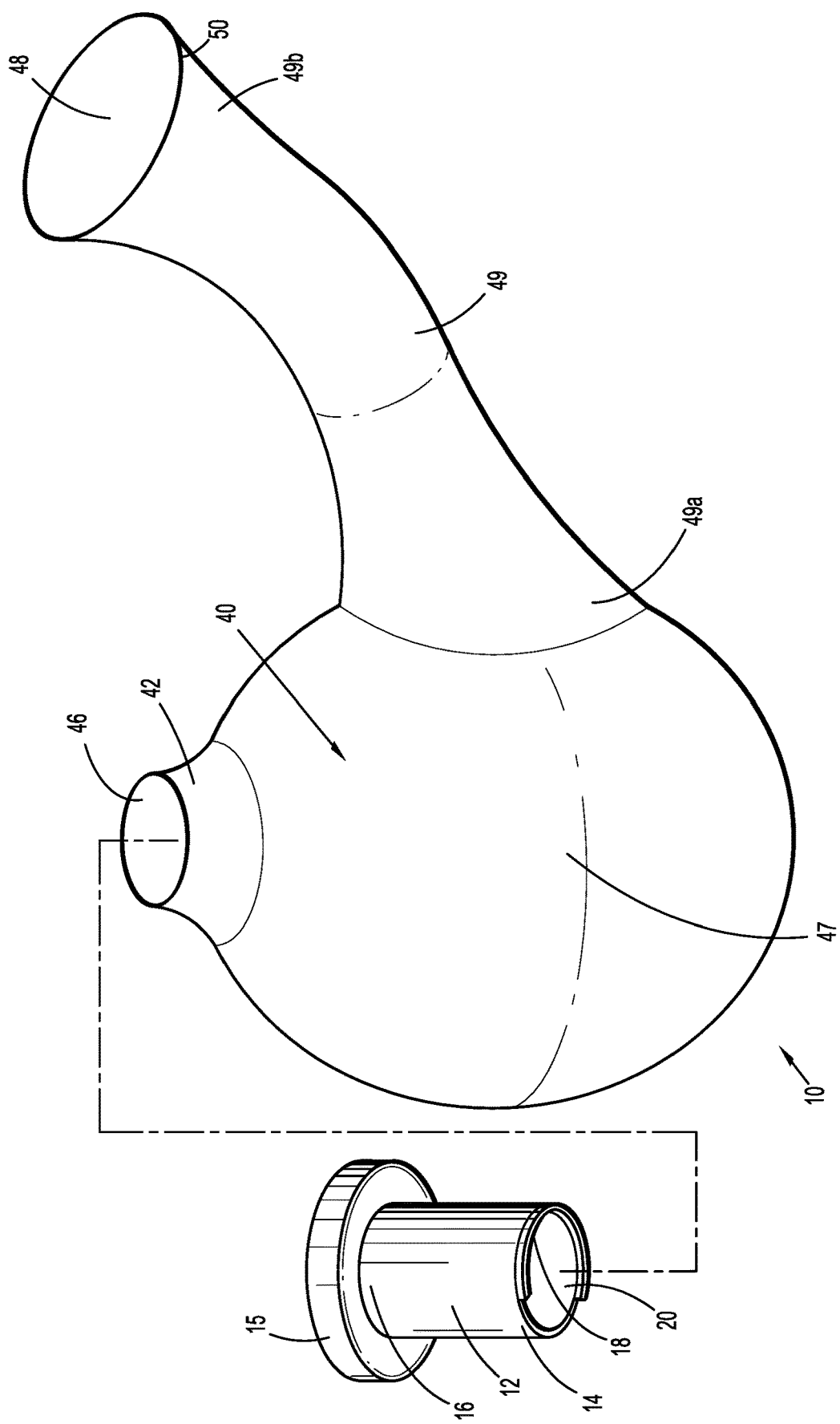
FIG. 2 is an exploded view of the specimen retrieval device shown in FIG. 1.

With reference to FIGS. 1-5, and initially with reference to FIGS. 1-2, a specimen retrieval device 10 according to an embodiment of the present disclosure is illustrated. The specimen retrieval device 10 includes a port 12 defining a longitudinal bore 20 and including a distal portion 14 and a proximal portion 16. In embodiments, the port 12 has a cutting element 18 at its distal portion 14, with a specimen bag 40 affixed to the distal portion 14 of the port 12. The port 12 may also include a flange 15 positioned about the proximal portion 16 and an end of the longitudinal bore 20. The flange 15 is configured to prevent the port 12 from passing into a patient's body cavity.

In embodiments, the port 12 of the specimen retrieval device 10 of the present disclosure is made of biocompatible materials within the purview of those skilled in the art, in embodiments, polymeric materials. For example, thermoplastic polyurethanes sold under the name PELLETHANE®, offer flexibility and a wide range of hardness. The port 12, for example, may be fabricated from PELLETHANE® 2363-80A, PELLETHANE® 2363-90A, PELLETHANE® 2363-55D, any combination thereof, or any alternatives within the purview of those skilled in the art.

The specimen bag 40 has two openings: a first opening 46 at a proximal portion 42 of the specimen bag 40 attached to the distal portion 14 of the port 12, and a second opening 48 of the specimen bag 40 spaced at a distance from the first opening 46. The first opening 46 at the proximal portion 42 of the specimen bag 40 is in fluid communication with the longitudinal bore 20 of the port 12, and, permits passage of surgical instruments (not shown) through the longitudinal bore 20 of the port 12 into a reservoir 47 defined by the specimen bag 40. The distal portion 14 of the port 12 may be received within the first opening 46 of the specimen bag 40 and attached to the proximal portion 42 of the specimen bag 40 by any suitable method, including adhesive bonding, welding, heat-sealing, combinations thereof, and the like.

As depicted in FIG. 1, the specimen bag 40 has a tubular trunk 49 that has a first end 49a that communicates with the reservoir 47 and a second end 49b that has a mouth 50 defining the second opening 48. The mouth 50 of the second opening 48 of the specimen bag 40 permits the introduction of surgical instruments/devices utilized in minimally invasive surgical procedures (not shown), including, for example, graspers, trocars, knives, scalpels, vacuum sources, inflation sources, or any other surgical device used by the clinician, into the reservoir 47 defined by the specimen bag 40.

The specimen bag 40 is made is resilient, antistatic, pyrogen-free, non-toxic, and sterilizable. In embodiments, materials used to form the port 12 described above may be used to form the specimen bag 40. In other embodiments, the specimen bag 40 is formed of materials that are different from those used to form the port 12. The specimen bag 40 may be opaque or clear.

The distal portion 14 of the port 12 may be attached to the cutting element 18 by any suitable method, including adhesive bonding, welding, heat-sealing, combinations thereof, and the like. The cutting element 18 is formed of a hard material such as a metal, which allows the cutting element 18 to cut tissue during placement of the port 12 into a patient's body (not shown) as well as cut tissue during removal of tissue from a patient's body after placement of the tissue into the specimen bag 40. In certain embodiments, the cutting element 18 is formed of a conductive material and is attached to electrical leads (not shown) such that electricity may be introduced to the cutting element 18, thereby facilitating cutting of tissue as part of an electrosurgical procedure. In these embodiments, the port 12 may be formed of an insulating or non-conductive material.

As depicted in FIGS. 1-5, in embodiments the cutting element 18 may be U-shaped. The U-shaped cutting element 18 may be a semi-circle or any similar u-shape having any desirable arc length. In other embodiments, the cutting element 18 may be of a different suitable shape, including, for example, circular or partially circular, i.e., a length longer than a semi-circle, but not a complete circle. Other suitable shapes include oblong, square, rectangular, or triangular, so long as the shape does not impede the attachment of the specimen bag 40 to the port 12 or the use of the port 12.

Kits of the present disclosure may include both the specimen retrieval device described herein, as well as trocars, scalpels, vacuum sources (tubes), inflation sources, additional ports, combinations thereof, and the like.

Figure 3:
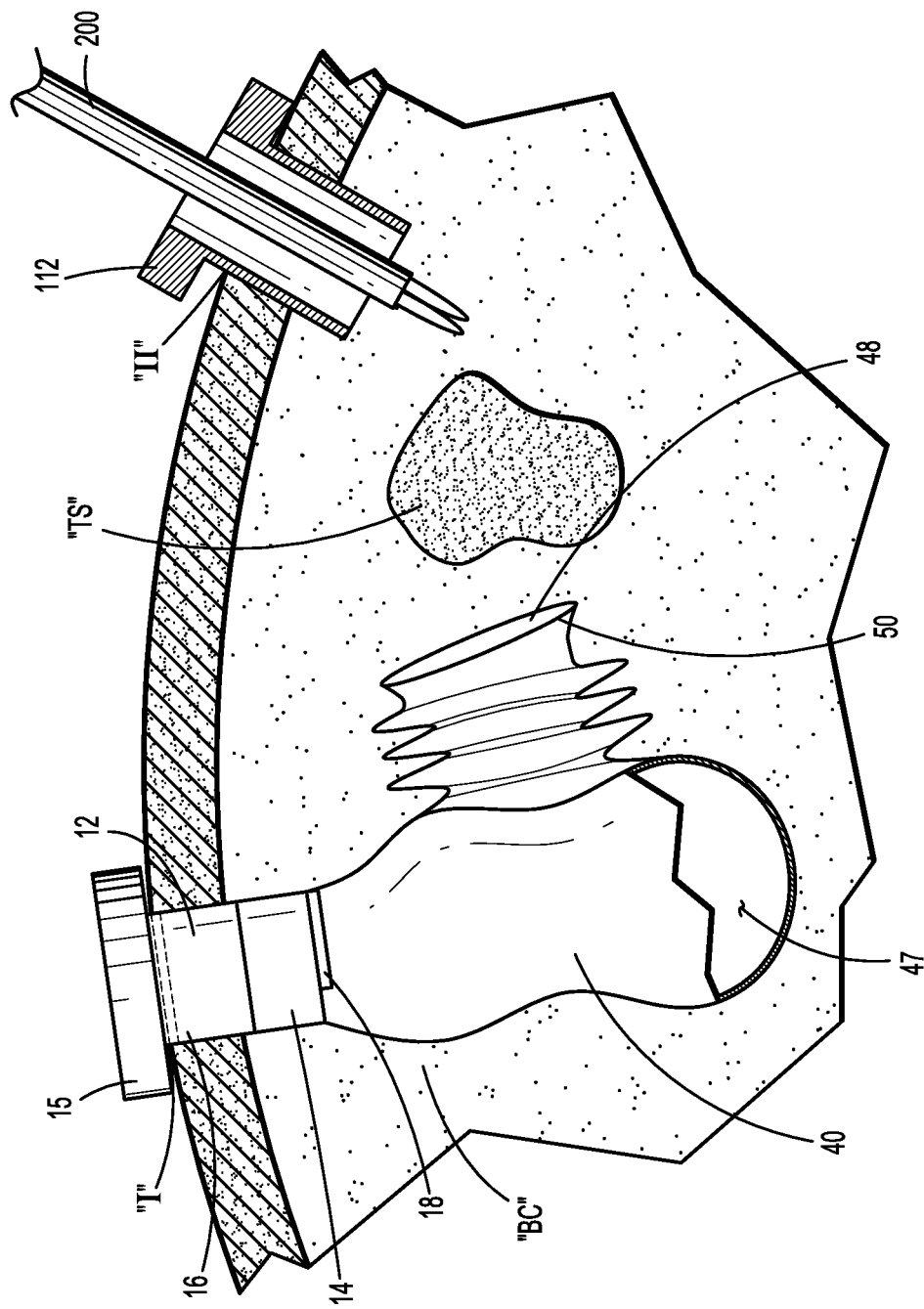
FIG. 3 is a perspective view of the specimen retrieval device shown in FIG. 1 positioned in a patient's body cavity, showing a second port to be used in conjunction with the specimen retrieval device.
Figure 4:
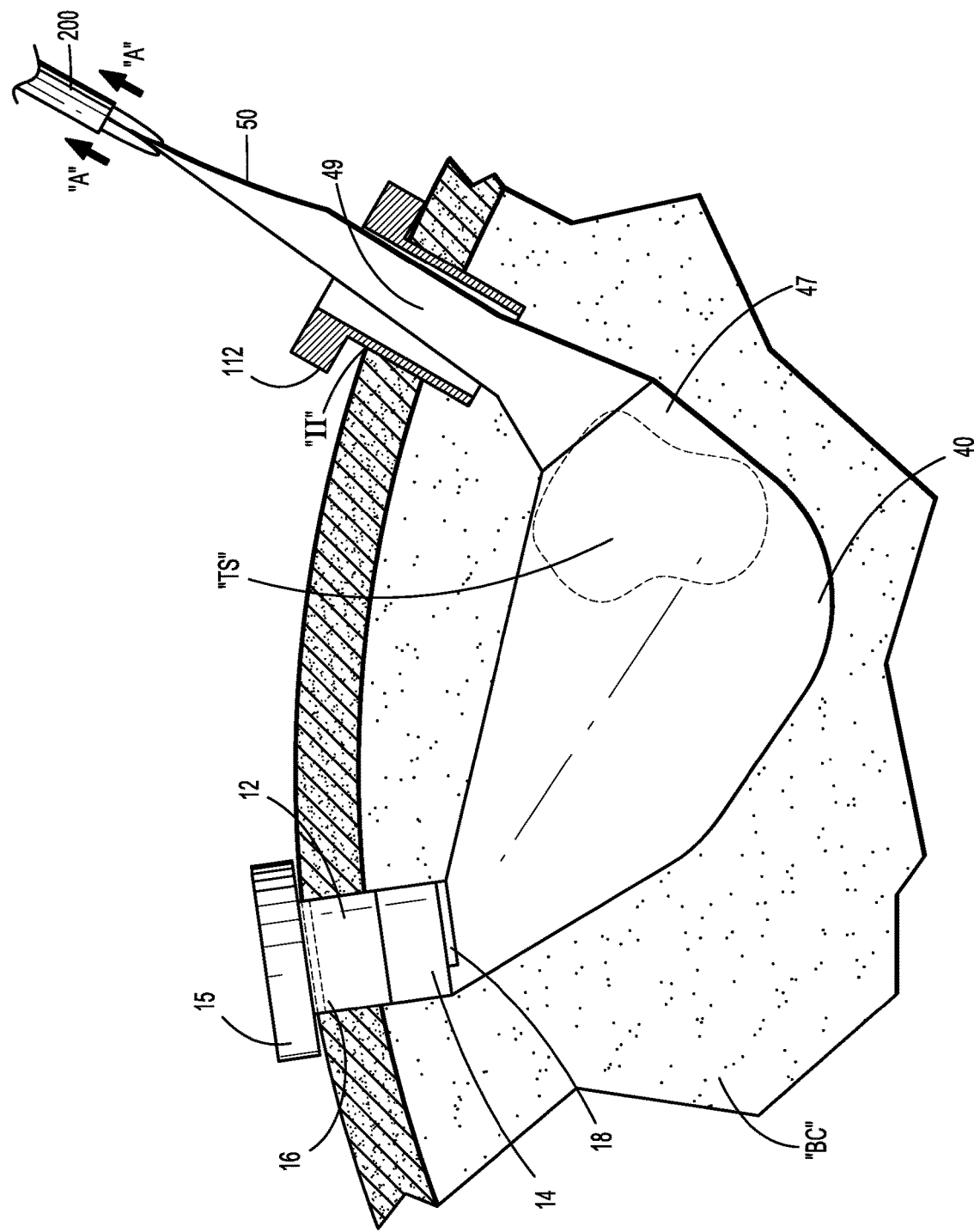
FIG. 4 is a perspective view of the specimen retrieval device shown in FIG. 3, after placement of a tissue specimen into the specimen bag.
Figure 5:
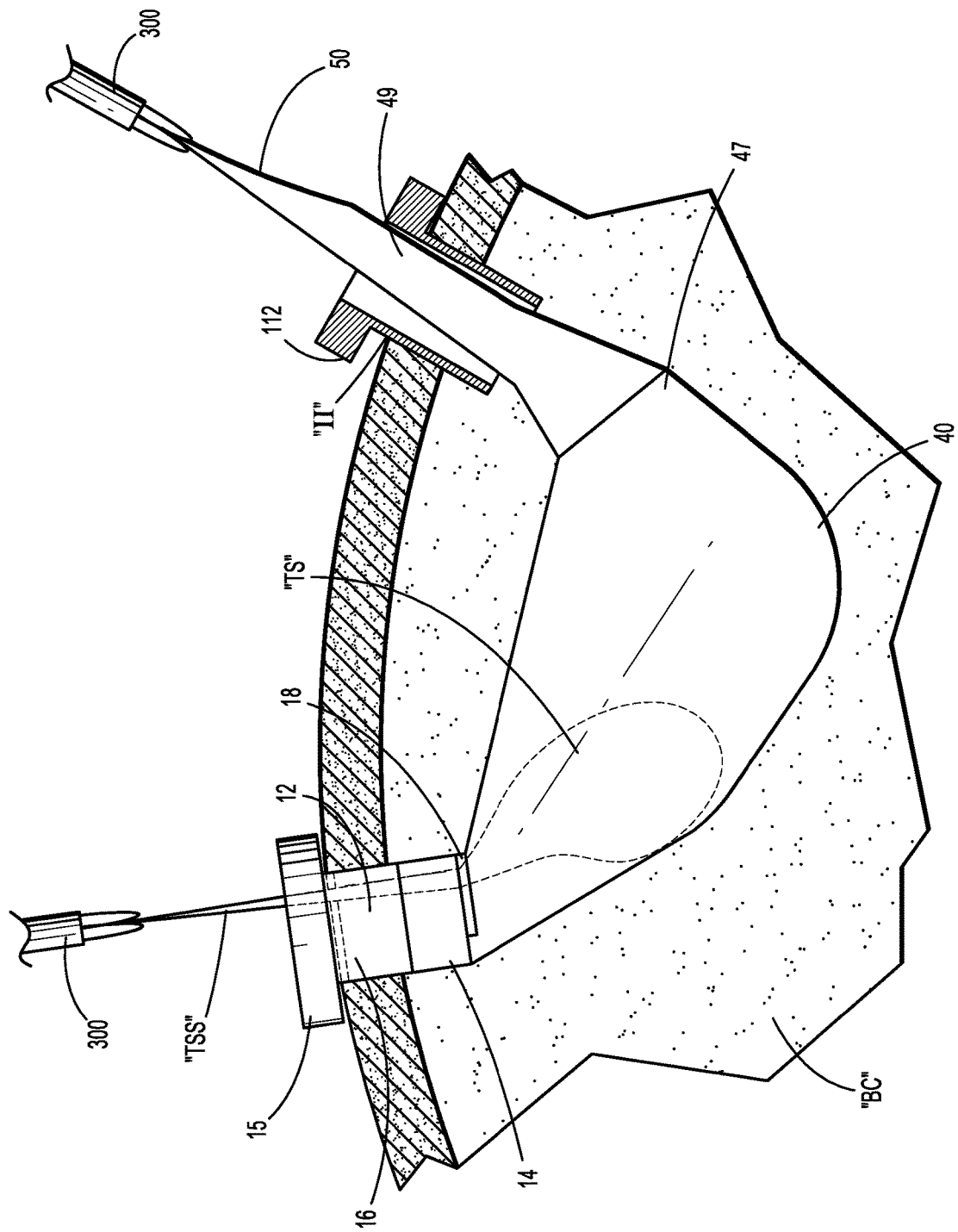
FIG. 5 is a perspective view of the specimen retrieval device shown in FIG. 4, as the tissue specimen is removed from the specimen bag through the specimen retrieval device.

In use, as depicted in FIGS. 3-5, the specimen retrieval device 10 is inserted through an incision "I" into a patient's body cavity "BC". The flange 15 prevents passage of the port 12 through the incision "I" into the body cavity "BC". The distal portion 14 of the port 12 of the specimen retrieval device 10, having the specimen bag 40 affixed thereto, is inserted through the incision "I". While no figure herein shows the actual insertion of the specimen bag, a detailed description of a method of inserting a specimen bag into a body cavity can be found, for example, in U.S. Pat. No. 5,647,372, the entire disclosure of which is incorporated by reference herein. A gas by way of an inflation source (not shown) can be supplied to the specimen bag 40 to increase a volume of the specimen bag 40.

With specific reference to FIG. 3, in embodiments, a kit of the present disclosure includes a second port 112 placed through a second incision "II" and a grasper 200 configured to pass through the second port 112. The grasper 200 facilitates placement of a tissue specimen "TS" within the reservoir 47 (FIG. 3) defined by the specimen bag 40 through the mouth 50 defining the second opening 48 of the specimen bag 40 (not shown).

As depicted in FIG. 4, after a tissue sample "TS" has been placed in the specimen bag 40, the grasper 200 is pulled proximally up (in the direction indicated by arrows "A") to pull the mouth 50 and the second opening 48 of the specimen bag 40 out of the body cavity "BC" through the second port 112, fully closing off the specimen bag 40 from the body cavity "BC".

As shown in FIG. 5, a second grasper 300 is then introduced through the port 12 and grasps the tissue specimen "TS." The second grasper 300 is pulled proximally to remove the tissue specimen "TS" from the specimen bag 40. As the tissue specimen "TS" passes through the distal portion 14 of the port 12, it comes into contact with the cutting element 18, which cuts the tissue specimen "TS," thereby permitting passage of the tissue sample out the proximal portion 16 of the port 12 in the form of elongated tissue specimen strips "TSS."

While not shown, it is to be appreciated that the port 12, the second grasper 300, or both, may be manipulated, for example by rotating the port 12 along its longitudinal axis and/or laterally deflecting the grasper 300 within the longitudinal bore 20 of the port 12, to enhance contact of the tissue specimen "TS" with the cutting element 18, thereby enhancing cutting of the tissue specimen "TS" and formation of elongated tissue specimen strips "TSS."

After the tissue specimen "TS" is entirely extracted from the specimen bag 40, the port 12 and the specimen bag 40 may be withdrawn out through the incision "I".

Alternatively, in some embodiments, small portions of tissue specimen "TS" may remain in the specimen bag 40 during removal of the specimen bag 40 through the incision "I" (not shown). Any such small portions of tissue specimen "TS" may then be removed from the specimen bag 40 for further examination and the specimen bag 40 may be discarded.

The specimen bags of the present disclosure may be useful for the removal of large tissue specimens from a body cavity. While previous specimen bags may be utilized to remove smaller tissue samples, the dual openings on the specimen bags of the present disclosure permit the construction of larger specimen bags in combination with ports that remain small to minimize trauma to a patient upon placement in an incision. The second opening of the specimen bag permits the introduction of tissue specimens therein, which may then be closed, permitting breaking down the tissue specimen as described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A specimen retrieval device, comprising:
   a port defining a longitudinal bore and a channel, the port possessing a proximal portion, a distal portion, and a cutting element fixedly attached to the distal portion; and
   a specimen bag defining a reservoir and having a first opening at a proximal portion of the specimen bag and a second opening spaced from the first opening, the first and second openings communicating with the reservoir, the first opening affixed to and in fluid communication with the distal portion of the port, and the second opening defined by a mouth of the specimen bag.

2. The specimen retrieval device of claim 1, wherein the cutting element possesses a shape including u-shaped, circular, partially circular, oblong, square, rectangular, or triangular.

3. The specimen retrieval device of claim 1, wherein the cutting element possesses a u-shape.

4. The specimen retrieval device of claim 1, wherein the cutting element is formed of an electrically conductive material and is attached to electrical leads.

5. The specimen retrieval device of claim 1, wherein the distal portion of the port is fixedly attached to the cutting element by a method including adhesive bonding, welding, heat-sealing, or combinations thereof.

6. The specimen retrieval device of claim 1, wherein the distal portion of the port is attached to the first opening of the specimen bag by a method including adhesive bonding, welding, heat-sealing, or combinations thereof.

7. The specimen retrieval device of claim 1, wherein the port has a proximal portion including a flange.

8. A kit comprising:
   the specimen retrieval device of claim 1; and
   at least one additional component including trocars, graspers, scalpels, vacuum tubes, inflation sources, or combinations thereof.

9. A method comprising:
   introducing a specimen retrieval device into a body opening such that a port of the specimen retrieval device extends through the body opening and a specimen bag having a first opening affixed to and in fluid communication with a distal portion of the port is positioned within a body cavity;
   passing a tissue specimen through a second opening of the specimen bag into the specimen bag, the second opening spaced from the first opening; and
   contacting the tissue specimen with a cutting element on the port as the tissue specimen is removed from the specimen bag through the port.

10. The method of claim 9, wherein the cutting element is formed of an electrically conductive material and attached to electrical leads which facilitate the cutting element cutting tissue.

11. The method of claim 9, wherein the cutting element possesses a shape including u-shaped, circular, partially circular, oblong, square, rectangular, or triangular.

12. The method of claim 9, wherein the cutting element possesses a u-shape.

13. The method of claim 9, wherein a grasper is used to contact the tissue specimen with the cutting element and remove the tissue specimen through the port.

14. The method of claim 13, further including manipulating the port, the grasper, or both, to preserve continuity of the tissue specimen as it passes through the port.

15. The method of claim 14, wherein the port is manipulated by rotating the port along its longitudinal axis.

16. The method of claim 14, wherein the grasper is manipulated by laterally deflecting the grasper within a longitudinal bore of the port.

17. The method of claim 9, further including, prior to removing the tissue specimen through the port:
- introducing a second port through a second body opening;
- introducing a grasper through the second port into the body cavity;
- grasping a mouth defining the second opening of the specimen bag with the grasper; and
- removing the mouth and the second opening of the specimen bag through the second port to close off the specimen bag from the body cavity.

* * * * *